United States Patent [19]

Rueb et al.

[11] Patent Number: 5,296,452
[45] Date of Patent: Mar. 22, 1994

[54] HERBICIDAL 3-(3,4,5,6-TETRAHYDROPHTHALIMIDO)-CINNAMIC ESTERS

[75] Inventors: Lothar Rueb, Speyer; Karl Eicken, Wachenheim; Karl-Otto Westphalen, Speyer; Bruno Wuerzer, Otterstadt, all of Fed. Rep. of Germany

[73] Assignee: BASF Aktiengesellschaft, Ludwigshafen, Fed. Rep. of Germany

[21] Appl. No.: 525,035

[22] Filed: May 18, 1990

[30] Foreign Application Priority Data

May 31, 1989 [DE] Fed. Rep. of Germany ....... 3917676
Sep. 22, 1989 [DE] Fed. Rep. of Germany ....... 3931615

[51] Int. Cl.$^5$ .................... A01N 43/38; C07D 209/04
[52] U.S. Cl. .................... 504/243; 548/490; 548/491
[58] Field of Search ............... 548/491; 71/96

[56] References Cited

FOREIGN PATENT DOCUMENTS 3724399 2/1989 Fed. Rep. of Germany .......... 71/96

OTHER PUBLICATIONS

Derwent Abstract, 86-078806 (Mitsubishi Chemical) Japanese Laid Open Application No. 27962/1986.

*Primary Examiner*—Dale R. Ore
*Attorney, Agent, or Firm*—Keil & Weinkauf

[57] ABSTRACT 3-(N-3,4,5,6-Tetrahydrophthalimido)-cinnamic esters of the general formula I where
n is 1 or 2 and the substituents have the following meanings:
$R^1$ is hydrogen or fluorine,
$R^2$ is halogen,
$R^3$ is hydrogen, halogen or $C_1$–$C_4$-alkyl,
$R^4$ is hydrogen, substituted or unsubstituted $C_1$–$C_6$-alkyl, $C_3$–$C_7$-cycloalkyl, $C_3$–$C_6$-alkenyl, $C_3$–$C_6$-alkynyl or benzyl,
R is $C_1$–$C_4$-alkyl, processes for their manufacture, and herbicidal agents containing them.

4 Claims, No Drawings

HERBICIDAL 3-(3,4,5,6-TETRAHYDROPHTHALIMIDO)-CINNAMIC ESTERS

The present invention relates to novel 3-(3,4,5,6-tetrahydrophthalimido)cinnamic esters of the general formula I

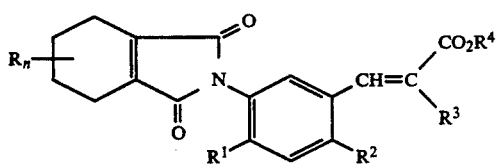

where $R^1$ is hydrogen or fluorine, $R^2$ is halogen, $R^3$ is hydrogen, halogen or $C_1-C_4$-alkyl, $R^4$ is hydrogen, $C_1-C_4$-alkyl which can be substituted by one or two $C_1-C_4$-alkoxy or $C_1-C_4$-alkylthio groups, or $C_3-C_7$-cycloalkyl, $C_3-C_6$-alkenyl, $C_3-C_6$-alkynyl or benzyl, R is $C_1-C_4$-alkyl, n is 1 or 2, and where formula I embraces all the isomeric forms of these compounds.

The present invention also relates to processes for the preparation of these compounds and to herbicidal agents and methods for the defoliation (desiccation) of cotton.

JP-A Kokai 27962/1986 discloses esters and amides of the structure I'

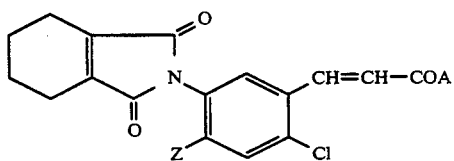

which, however, are unsatisfactory in terms of the application rates required. Hence it was an object of the present invention to prepare particularly active herbicidal compounds.

We have now found that the 3-(3,4,5,6-tetrahydrophthalimido)cinnamic esters of the formula I defined in the first paragraph have good herbicidal activity even at low application rates.

The compounds I are obtained, for example, by reacting a cinnamic acid derivative II in an aprotic polar organic solvent in a conventional manner (Houben-Weyl Vol. X/2,747) in the presence of a base with an alcohol of the formula III, subsequently reducing the resulting nitrocinnamic ester IV to the amino compound V, and condensing V with a tetrahydrophthalic anhydride.

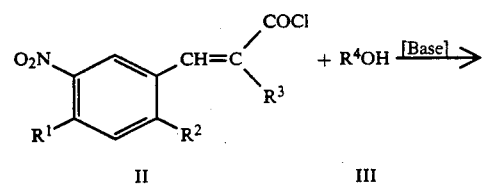

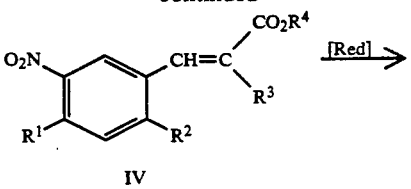

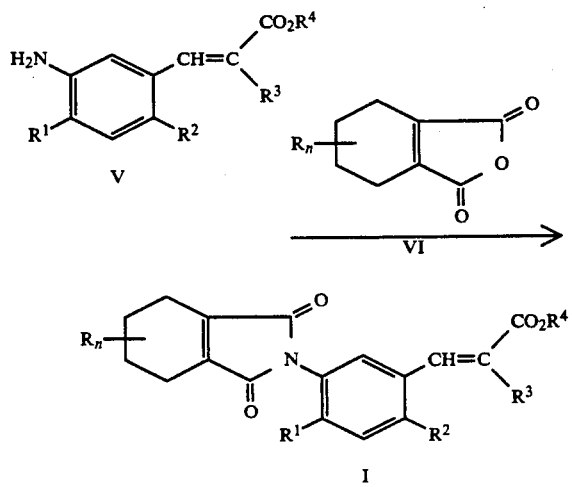

The solvents mainly used for the reaction of II with III are high-boiling hydrocarbons such as xylene and toluene, esters such as ethyl acetate and ethers such as dioxane and tetrahydrofuran.

The reaction is usually carried out at from $-10°$ C. to $200°$ C., preferably at from $0°$ to $150°$ C.

Examples of bases suitable for this reaction are tertiary amines such as triethylamine and pyridine, or inorganic salts such as sodium hydroxide, potassium hydroxide and potassium carbonate.

The aniline derivatives of the formula V can be obtained in a conventional manner from the corresponding nitrophenyl derivatives IV, either by reduction with inorganic compounds such as tin(II) salts or iron or, if $R^3$ is not bromine or chlorine, by catalytic hydrogenation on metal catalysts such as Raney nickel, palladium and platinum.

The reduction is generally carried out in protic polar solvents such as glacial acetic acid at from $0°$ C. to $150°$ C., preferably $20°$ C. to $100°$ C. The solvent used for the catalytic hydrogenation is, for example, methanol or tetrahydrofuran. The reaction is then carried out at from $0°$ C. to $100°$ C. under a pressure of from 1 to 100 atm of hydrogen.

Used for the condensation of the 3,4,5,6-tetrahydrophthalic anhydride of the formula VI with a 3-aminocinnamic ester of the formula V are inert organic solvents such as lower alkanoic acids such as acetic acid, propionic acid and isobutyric acid, and the esters of these acids such as ethyl acetate, high-boiling hydrocarbons such as toluene and xylene and/or dimethylformamide. The reaction is usually carried out at from $25°$ C. to the boiling point of the reaction mixture, preferably from $50°$ to $140°$ C. When an aprotic solvent is used, it is advisable to remove the water continuously.

If $R^3$ is chlorine or bromine, the compounds I can also be prepared by halogenating a nitrocinnamic ester of the formula IVb in an inert organic solvent with the appropriate halogen to give the nitrocinnamic ester of the formula IV, and subsequently treating the latter as described above.

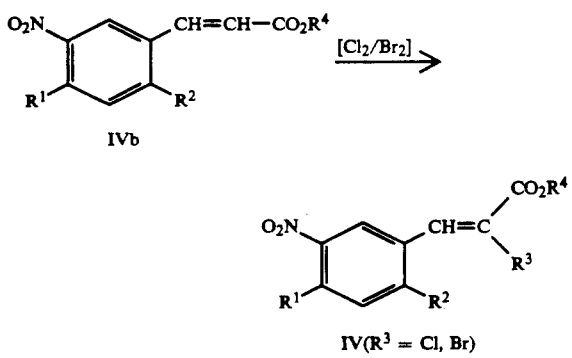

The halogenation is usually carried out at from 0° to 60° C., preferably 15° to 40° C.

Examples of suitable solvents are methylene chloride, chloroform, tetrachloromethane, 1,1,1-trichloroethane and chlorobenzene, with methylene chloride, chloroform and 1,1,1-trichloroethane being preferred.

The compounds of the formula I are, however, also obtained by reacting a suitably substituted aldehyde IX with an ylide of the formula X in a conventional manner, e.g. under the conditions described in Synthesis 10 (1984) 862, in a solvent at from room temperature to the boiling point of the solvent.

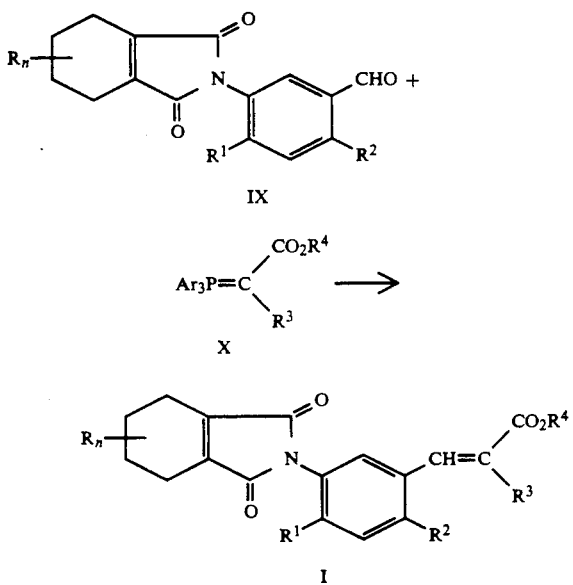

Ar in formula X is unsubstituted or substituted aryl, with phenyl generally being preferred.

Examples of suitable solvents are toluene, tetrahydrofuran, dimethylformamide, dimethyl sulfoxide and methanol.

The required triarylphosphoranes X can be obtained by processes similar to those described in Chem. Ber. 95 (1962) 3003.

The required aldehyde IX is obtained, for example, by condensing the aniline VIII with the anhydride VI. When lower carboxylic acids such as acetic or propionic acid are used for this, there is simultaneous cleavage of the acetal.

The following substituents are preferred with a view to the intended use of the compounds I as herbicides:

$R^1$: hydrogen and fluorine, $R^2$: halogen such as fluorine, chlorine and bromine, especially chlorine, $R^3$: hydrogen; halogen as mentioned for $R^2$, especially chlorine and bromine; alkyl such as methyl, ethyl, propyl, 1-methylethyl, butyl, 1-methylpropyl, 2-methylpropyl and 1,1-dimethylethyl, especially methyl and ethyl, $R^4$: hydrogen, alkyl as mentioned for $R^3$, and n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl and 1-ethyl-2-methylpropyl, especially methyl, ethyl, propyl and iso-propyl, it being possible for each alkyl to be substituted by one or two $C_1$-$C_4$-alkoxy or $C_1$-$C_4$-alkylthio groups, resulting in alkoxyalkyl groups such as methoxymethyl, 2-methoxyethyl, 2-methoxypropyl, 3-methoxypropyl, 2-methoxy-1-methylethyl, ethoxymethyl, 2-ethoxyethyl, 2-ethoxypropyl, 3-ethoxypropyl, 2-ethoxy-1-methylethyl and 1-ethoxy-1-methylethyl, especially methoxyethyl and ethoxyethyl, and alkylthioalkyl groups, especially methylthioethyl and ethylthioethyl; cycloalkyl such as cyclopropyl, cyclobutyl, cyclopentyl, cyclohexyl and cycloheptyl; alkenyl such as 2-propenyl, 2-butenyl, 3-butenyl, 1-methyl-2-propenyl, 2-methyl-2-propenyl, 2-pentenyl, 1-methyl-2-butenyl, 2-methyl-2-butenyl,3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1, 3-dimethyl-2-butenyl, 1, 2-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, or corresponding alkenyloxy, alkynyl, such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1, 1-dimethyl-2-propynyl, 1-ethyl-2-propynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, or corresponding alkynyloxy, or benzyl.

Examples of very active compounds I are listed in Tables A and B which follow.

TABLE A

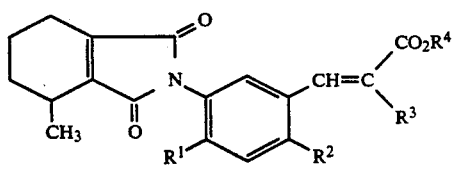

Ia

| R¹ | R² | R³ | R⁴ |
|---|---|---|---|
| H | Cl | H | H |
| F | Cl | H | H |
| H | Br | H | H |
| F | Br | H | H |
| H | Cl | Cl | H |
| F | Cl | Cl | H |
| H | Br | Cl | H |
| F | Br | Cl | H |
| H | Cl | Br | H |
| F | Cl | Br | H |
| H | Br | Br | H |
| F | Br | Br | H |
| H | Cl | CH₃ | H |
| F | Cl | CH₃ | H |
| H | Br | CH₃ | H |
| F | Br | CH₃ | H |
| H | Cl | CH₂CH₃ | H |
| F | Cl | CH₂CH₃ | H |
| H | Br | CH₂CH₃ | H |
| F | Br | CH₂CH₃ | H |
| H | Cl | H | CH₃ |
| F | Cl | H | CH₃ |
| H | Br | H | CH₃ |
| F | Br | H | CH₃ |
| H | Cl | Cl | CH₃ |
| F | Cl | Cl | CH₃ |
| H | Br | Cl | CH₃ |
| F | Br | Cl | CH₃ |
| H | Cl | Br | CH₃ |
| F | Cl | Br | CH₃ |
| H | Br | Br | CH₃ |
| F | Br | Br | CH₃ |
| H | Cl | CH₃ | CH₃ |
| F | Cl | CH₃ | CH₃ |
| H | Br | CH₃ | CH₃ |
| F | Br | CH₃ | CH₃ |
| H | Cl | CH₂CH₃ | CH₃ |
| F | Cl | CH₂CH₃ | CH₃ |
| H | Br | CH₂CH₃ | CH₃ |
| F | Br | CH₂CH₃ | CH₃ |
| H | Cl | H | CH₂CH₃ |
| F | Cl | H | CH₂CH₃ |
| H | Br | H | CH₂CH₃ |
| F | Br | H | CH₂CH₃ |
| H | Cl | Cl | CH₂CH₃ |
| F | Cl | Cl | CH₂CH₃ |
| H | Br | Cl | CH₂CH₃ |
| F | Br | Cl | CH₂CH₃ |
| H | Cl | Br | CH₂CH₃ |
| F | Cl | Br | CH₂CH₃ |
| H | Br | Br | CH₂CH₃ |
| F | Br | Br | CH₂CH₃ |
| H | Cl | CH₃ | CH₂CH₃ |
| F | Cl | CH₃ | CH₂CH₃ |
| H | Br | CH₃ | CH₂CH₃ |
| F | Br | CH₃ | CH₂CH₃ |
| H | Cl | CH₂CH₃ | CH₂CH₃ |
| F | Cl | CH₂CH₃ | CH₂CH₃ |
| H | Br | CH₂CH₃ | CH₂CH₃ |
| F | Br | CH₂CH₃ | CH₂CH₃ |
| H | Cl | H | (CH₂)₂CH₃ |
| F | Cl | H | (CH₂)₂CH₃ |
| H | Cl | Cl | (CH₂)₂CH₃ |
| F | Cl | Cl | (CH₂)₂CH₃ |
| H | Cl | Br | (CH₂)₂CH₃ |
| F | Cl | Br | (CH₂)₂CH₃ |
| H | Cl | CH₃ | (CH₂)₂CH₃ |
| F | Cl | CH₃ | (CH₂)₂CH₃ |
| H | Cl | CH₂CH₃ | (CH₂)₂CH₃ |
| F | Cl | CH₂CH₃ | (CH₂)₂CH₃ |
| H | Cl | H | CH(CH₃)₂ |
| F | Cl | H | CH(CH₃)₂ |

TABLE A-continued

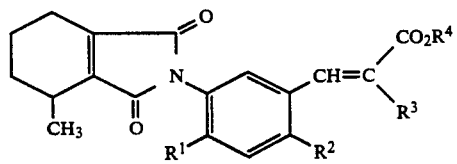

Ia

| R¹ | R² | R³ | R⁴ |
|---|---|---|---|
| H | Cl | Cl | CH(CH₃)₂ |
| F | Cl | Cl | CH(CH₃)₂ |
| H | Cl | Br | CH(CH₃)₂ |
| F | Cl | Br | CH(CH₃)₂ |
| H | Cl | CH₃ | CH(CH₃)₂ |
| F | Cl | CH₃ | CH(CH₃)₂ |
| H | Cl | CH₂CH₃ | CH(CH₃)₂ |
| F | Cl | CH₂CH₃ | CH(CH₃)₂ |
| H | Cl | H | (CH₂)₃CH₃ |
| F | Cl | H | (CH₂)₃CH₃ |
| H | Cl | Cl | (CH₂)₃CH₃ |
| F | Cl | Cl | (CH₂)₃CH₃ |
| H | Cl | Br | (CH₂)₃CH₃ |
| F | Cl | Br | (CH₂)₃CH₃ |
| H | Cl | CH₃ | (CH₂)₃CH₃ |
| F | Cl | CH₃ | (CH₂)₃CH₃ |
| H | Cl | CH₂CH₃ | (CH₂)₃CH₃ |
| F | Cl | CH₂CH₃ | (CH₂)₃CH₃ |
| H | Cl | H | CH₂CH(CH₃)₂ |
| F | Cl | H | CH₂CH(CH₃)₂ |
| H | Cl | Cl | CH₂CH(CH₃)₂ |
| F | Cl | Cl | CH₂CH(CH₃)₂ |
| H | Cl | Br | CH₂CH(CH₃)₂ |
| F | Cl | Br | CH₂CH(CH₃)₂ |
| H | Cl | CH₃ | CH₂CH(CH₃)₂ |
| F | Cl | CH₃ | CH₂CH(CH₃)₂ |
| H | Cl | CH₂CH₃ | CH₂CH(CH₃)₂ |
| F | Cl | CH₂CH₃ | CH₂CH(CH₃)₂ |
| H | Cl | H | (CH₂)₄CH₃ |
| F | Cl | H | (CH₂)₄CH₃ |
| H | Cl | Cl | (CH₂)₄CH₃ |
| F | Cl | Cl | (CH₂)₄CH₃ |
| H | Cl | Br | (CH₂)₄CH₃ |
| F | Cl | Br | (CH₂)₄CH₃ |
| H | Cl | CH₃ | (CH₂)₄CH₃ |
| F | Cl | CH₃ | (CH₂)₄CH₃ |
| H | Cl | CH₂CH₃ | (CH₂)₄CH₃ |
| F | Cl | CH₂CH₃ | (CH₂)₄CH₃ |
| H | Cl | H | (CH₂)₂CH(CH₃)₂ |
| F | Cl | H | (CH₂)₂CH(CH₃)₂ |
| H | Cl | Cl | (CH₂)₂CH(CH₃)₂ |
| F | Cl | Cl | (CH₂)₂CH(CH₃)₂ |
| H | Cl | Br | (CH₂)₂CH(CH₃)₂ |
| F | Cl | Br | (CH₂)₂CH(CH₃)₂ |
| H | Cl | CH₃ | (CH₂)₂CH(CH₃)₂ |
| F | Cl | CH₃ | (CH₂)₂CH(CH₃)₂ |
| H | Cl | CH₂CH₃ | (CH₂)₂CH(CH₃)₂ |
| F | Cl | CH₂CH₃ | (CH₂)₂CH(CH₃)₂ |
| H | Cl | H | (CH₂)₂OCH₃ |
| F | Cl | H | (CH₂)₂OCH₃ |
| H | Cl | Cl | (CH₂)₂OCH₃ |
| F | Cl | Cl | (CH₂)₂OCH₃ |
| H | Cl | Br | (CH₂)₂OCH₃ |
| F | Cl | Br | (CH₂)₂OCH₃ |
| H | Cl | CH₃ | (CH₂)₂OCH₃ |
| F | Cl | CH₃ | (CH₂)₂OCH₃ |
| H | Cl | CH₂CH₃ | (CH₂)₂OCH₃ |
| F | Cl | CH₂CH₃ | (CH₂)₂OCH₃ |
| H | Cl | H | CH(CH₃)CH₂OCH₃ |
| F | Cl | H | CH(CH₃)CH₂OCH₃ |
| H | Cl | Cl | CH(CH₃)CH₂OCH₃ |
| F | Cl | Cl | CH(CH₃)CH₂OCH₃ |
| H | Cl | Br | CH(CH₃)CH₂OCH₃ |
| F | Cl | Br | CH(CH₃)CH₂OCH₃ |
| H | Cl | CH₃ | CH(CH₃)CH₂OCH₃ |
| F | Cl | CH₃ | CH(CH₃)CH₂OCH₃ |
| H | Cl | CH₂CH₃ | CH(CH₃)CH₂OCH₃ |
| F | Cl | CH₂CH₃ | CH(CH₃)CH₂OCH₃ |
| H | Cl | H | CH₂CH=CH₂ |
| F | Cl | H | CH₂CH=CH₂ |
| H | Cl | Cl | CH₂CH=CH₂ |
| F | Cl | Cl | CH₂CH=CH₂ |

TABLE A-continued

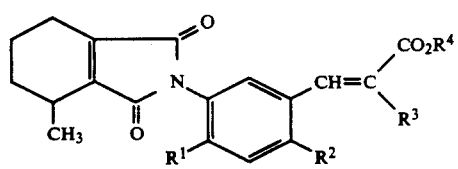

Ia

| R¹ | R² | R³ | R⁴ |
|---|---|---|---|
| H | Cl | Br | CH₂CH=CH₂ |
| F | Cl | Br | CH₂CH=CH₂ |
| H | Cl | CH₃ | CH₂CH=CH₂ |
| F | Cl | CH₃ | CH₂CH=CH₂ |
| H | Cl | CH₂CH₃ | CH₂CH=CH₂ |
| F | Cl | CH₂CH₃ | CH₂CH=CH₂ |
| H | Cl | H | CH₂CH=CHCH₃ |
| F | Cl | H | CH₂CH=CHCH₃ |
| H | Cl | Cl | CH₂CH=CHCH₃ |
| F | Cl | Cl | CH₂CH=CHCH₃ |
| H | Cl | Br | CH₂CH=CHCH₃ |
| F | Cl | Br | CH₂CH=CHCH₃ |
| H | Cl | CH₃ | CH₂CH=CHCH₃ |
| F | Cl | CH₃ | CH₂CH=CHCH₃ |
| H | Cl | CH₂CH₃ | CH₂CH=CHCH₃ |
| F | Cl | CH₂CH₃ | CH₂CH=CHCH₃ |
| H | Cl | H | CH₂C≡CH |
| F | Cl | H | CH₂C≡CH |
| H | Cl | Cl | CH₂C≡CH |
| F | Cl | Cl | CH₂C≡CH |
| H | Cl | Br | CH₂C≡CH |
| F | Cl | Br | CH₂C≡CH |
| H | Cl | CH₃ | CH₂C≡CH |
| F | Cl | CH₃ | CH₂C≡CH |
| H | Cl | CH₂CH₃ | CH₂C≡CH |
| F | Cl | CH₂CH₃ | CH₂C≡CH |
| H | Cl | H | CH₂C≡CCH₃ |
| F | Cl | H | CH₂C≡CCH₃ |
| H | Cl | Cl | CH₂C≡CCH₃ |
| F | Cl | Cl | CH₂C≡CCH₃ |
| H | Cl | Br | CH₂C≡CCH₃ |
| F | Cl | Br | CH₂C≡CCH₃ |
| H | Cl | CH₃ | CH₂C≡CCH₃ |
| F | Cl | CH₃ | CH₂C≡CCH₃ |
| H | Cl | CH₂CH₃ | CH₂C≡CCH₃ |
| F | Cl | CH₂CH₃ | CH₂C≡CCH₃ |
| H | Cl | H | CH₂Ph |
| F | Cl | H | CH₂Ph |
| H | Cl | Cl | CH₂Ph |
| F | Cl | Cl | CH₂Ph |
| H | Cl | Br | CH₂Ph |
| F | Cl | Br | CH₂Ph |
| H | Cl | CH₃ | CH₂Ph |
| F | Cl | CH₃ | CH₂Ph |
| H | Cl | CH₂CH₃ | CH₂Ph |
| F | Cl | CH₂CH₃ | CH₂Ph |
| H | F | Cl | CH₃ |
| H | F | Br | CH₃ |
| H | F | CH₃ | CH₃ |
| H | F | Cl | CH₂CH₃ |
| H | F | Br | CH₂CH₃ |
| H | F | CH₃ | CH₂CH₃ |
| H | F | Cl | (CH₂)₂CH₃ |
| H | F | Br | (CH₂)₂CH₃ |
| H | F | CH₃ | (CH₂)₂CH₃ |
| H | F | Cl | CH(CH₃)₂ |
| H | F | Br | CH(CH₃)₂ |
| H | F | CH₃ | CH(CH₃)₂ |
| H | F | Cl | (CH₂)₃CH₃ |
| H | F | Br | (CH₂)₃CH₃ |
| H | F | CH₃ | (CH₂)₃CH₃ |
| H | F | Cl | CH₂CH(CH₃)₂ |
| H | F | Br | CH₂CH(CH₃)₂ |
| H | F | CH₃ | CH₂CH(CH₃)₂ |
| H | F | Cl | (CH₂)₄CH₃ |
| H | F | Br | (CH₂)₄CH₃ |
| H | F | CH₃ | (CH₂)₄CH₃ |
| H | F | Cl | (CH₂)₂CH(CH₃)₂ |
| H | F | Br | (CH₂)₂CH(CH₃)₂ |
| H | F | CH₃ | (CH₂)₂CH(CH₃)₂ |
| H | F | Cl | (CH₂)₂OCH₃ |
| H | F | Br | (CH₂)₂OCH₃ |

TABLE A-continued

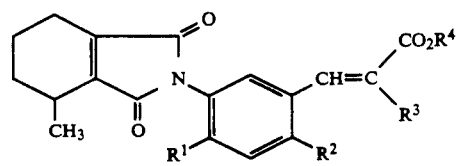

Ia

| R¹ | R² | R³ | R⁴ |
|---|---|---|---|
| H | F | CH₃ | (CH₂)₂OCH₃ |
| H | F | Cl | CH(CH₃)CH₂OCH₃ |
| H | F | Br | CH(CH₃)CH₂OCH₃ |
| H | F | CH₃ | CH(CH₃)CH₂OCH₃ |
| H | F | Cl | CH₂CH=CH₂ |
| H | F | Br | CH₂CH=CH₂ |
| H | F | CH₃ | CH₂CH=CH₂ |
| H | F | Cl | CH₂CH=CHCH₃ |
| H | F | Br | CH₂CH=CHCH₃ |
| H | F | CH₃ | CH₂CH=CHCH₃ |
| H | F | Cl | CH₂C≡CH |
| H | F | Br | CH₂C≡CH |
| H | F | CH₃ | CH₂C≡CH |
| H | F | Cl | CH₂C≡CCH₃ |
| H | F | Br | CH₂C≡CCH₃ |
| H | F | CH₃ | CH₂C≡CCH₃ |
| H | F | Cl | CH₂Ph |
| H | F | Br | CH₂Ph |
| H | F | CH₃ | CH₂Ph |

TABLE B

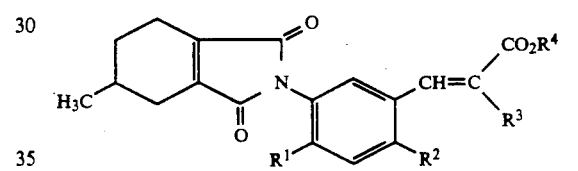

Ib

| R¹ | R² | R³ | R⁴ |
|---|---|---|---|
| H | Cl | H | H |
| F | Cl | H | H |
| H | Br | H | H |
| F | Br | H | H |
| H | Cl | Cl | H |
| F | Cl | Cl | H |
| H | Br | Cl | H |
| F | Br | Cl | H |
| H | Cl | Br | H |
| F | Cl | Br | H |
| H | Br | Br | H |
| F | Br | Br | H |
| H | Cl | CH₃ | H |
| F | Cl | CH₃ | H |
| H | Br | CH₃ | H |
| F | Br | CH₃ | H |
| H | Cl | CH₂CH₃ | H |
| F | Cl | CH₂CH₃ | H |
| H | Br | CH₂CH₃ | H |
| F | Br | CH₂CH₃ | H |
| H | Cl | H | CH₃ |
| F | Cl | H | CH₃ |
| H | Br | H | CH₃ |
| F | Br | H | CH₃ |
| H | Cl | Cl | CH₃ |
| F | Cl | Cl | CH₃ |
| H | Br | Cl | CH₃ |
| F | Br | Cl | CH₃ |
| H | Cl | Br | CH₃ |
| F | Cl | Br | CH₃ |
| H | Br | Br | CH₃ |
| F | Br | Br | CH₃ |
| H | Cl | CH₃ | CH₃ |
| F | Cl | CH₃ | CH₃ |
| H | Br | CH₃ | CH₃ |
| F | Br | CH₃ | CH₃ |
| H | Cl | CH₂CH₃ | CH₃ |
| F | Cl | CH₂CH₃ | CH₃ |

TABLE B-continued

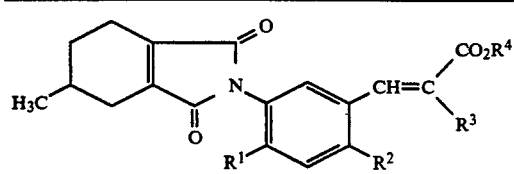

| R¹ | R² | R³ | R⁴ |
|---|---|---|---|
| H | Br | CH₂CH₃ | CH₃ |
| F | Br | CH₂CH₃ | CH₃ |
| H | Cl | H | CH₂CH₃ |
| F | Cl | H | CH₂CH₃ |
| H | Br | H | CH₂CH₃ |
| F | Br | H | CH₂CH₃ |
| H | Cl | Cl | CH₂CH₃ |
| F | Cl | Cl | CH₂CH₃ |
| H | Br | Cl | CH₂CH₃ |
| F | Br | Cl | CH₂CH₃ |
| H | Cl | Br | CH₂CH₃ |
| F | Cl | Br | CH₂CH₃ |
| H | Br | Br | CH₂CH₃ |
| F | Br | Br | CH₂CH₃ |
| H | Cl | CH₃ | CH₂CH₃ |
| F | Cl | CH₃ | CH₂CH₃ |
| H | Br | CH₃ | CH₂CH₃ |
| F | Br | CH₃ | CH₂CH₃ |
| H | Cl | CH₂CH₃ | CH₂CH₃ |
| F | Cl | CH₂CH₃ | CH₂CH₃ |
| H | Br | CH₂CH₃ | CH₂CH₃ |
| F | Br | CH₂CH₃ | CH₂CH₃ |
| H | Cl | H | (CH₂)₂CH₃ |
| F | Cl | H | (CH₂)₂CH₃ |
| H | Cl | Cl | (CH₂)₂CH₃ |
| F | Cl | Cl | (CH₂)₂CH₃ |
| H | Cl | Br | (CH₂)₂CH₃ |
| F | Cl | Br | (CH₂)₂CH₃ |
| H | Cl | CH₃ | (CH₂)₂CH₃ |
| F | Cl | CH₃ | (CH₂)₂CH₃ |
| H | Cl | CH₂CH₃ | (CH₂)₂CH₃ |
| F | Cl | CH₂CH₃ | (CH₂)₂CH₃ |
| H | Cl | H | CH(CH₃)₂ |
| F | Cl | H | CH(CH₃)₂ |
| H | Cl | Cl | CH(CH₃)₂ |
| F | Cl | Cl | CH(CH₃)₂ |
| H | Cl | Br | CH(CH₃)₂ |
| F | Cl | Br | CH(CH₃)₂ |
| H | Cl | CH₃ | CH(CH₃)₂ |
| F | Cl | CH₃ | CH(CH₃)₂ |
| H | Cl | CH₂CH₃ | CH(CH₃)₂ |
| F | Cl | CH₂CH₃ | CH(CH₃)₂ |
| H | Cl | H | (CH₂)₃CH₃ |
| F | Cl | H | (CH₂)₃CH₃ |
| H | Cl | Cl | (CH₂)₃CH₃ |
| F | Cl | Cl | (CH₂)₃CH₃ |
| H | Cl | Br | (CH₂)₃CH₃ |
| F | Cl | Br | (CH₂)₃CH₃ |
| H | Cl | CH₃ | (CH₂)₃CH₃ |
| F | Cl | CH₃ | (CH₂)₃CH₃ |
| H | Cl | CH₂CH₃ | (CH₂)₃CH₃ |
| F | Cl | CH₂CH₃ | (CH₂)₃CH₃ |
| H | Cl | H | CH₂CH(CH₃)₂ |
| F | Cl | H | CH₂CH(CH₃)₂ |
| H | Cl | Cl | CH₂CH(CH₃)₂ |
| F | Cl | Cl | CH₂CH(CH₃)₂ |
| H | Cl | Br | CH₂CH(CH₃)₂ |
| F | Cl | Br | CH₂CH(CH₃)₂ |
| H | Cl | CH₃ | CH₂CH(CH₃)₂ |
| F | Cl | CH₃ | CH₂CH(CH₃)₂ |
| H | Cl | CH₂CH₃ | CH₂CH(CH₃)₂ |
| F | Cl | CH₂CH₃ | CH₂CH(CH₃)₂ |
| H | Cl | H | (CH₂)₄CH₃ |
| F | Cl | H | (CH₂)₄CH₃ |
| H | Cl | Cl | (CH₂)₄CH₃ |
| F | Cl | Cl | (CH₂)₄CH₃ |
| H | Cl | Br | (CH₂)₄CH₃ |
| F | Cl | Br | (CH₂)₄CH₃ |
| H | Cl | CH₃ | (CH₂)₄CH₃ |
| F | Cl | CH₃ | (CH₂)₄CH₃ |
| H | Cl | CH₂CH₃ | (CH₂)₄CH₃ |
| F | Cl | CH₂CH₃ | (CH₂)₄CH₃ |
| H | Cl | H | (CH₂)₂CH(CH₃)₂ |
| F | Cl | H | (CH₂)₂CH(CH₃)₂ |
| H | Cl | Cl | (CH₂)₂CH(CH₃)₂ |
| F | Cl | Cl | (CH₂)₂CH(CH₃)₂ |
| H | Cl | Br | (CH₂)₂CH(CH₃)₂ |
| F | Cl | Br | (CH₂)₂CH(CH₃)₂ |
| H | Cl | CH₃ | (CH₂)₂CH(CH₃)₂ |
| F | Cl | CH₃ | (CH₂)₂CH(CH₃)₂ |
| H | Cl | CH₂CH₃ | (CH₂)₂CH(CH₃)₂ |
| F | Cl | CH₂CH₃ | (CH₂)₂CH(CH₃)₂ |
| H | Cl | H | (CH₂)₂OCH₃ |
| F | Cl | H | (CH₂)₂OCH₃ |
| H | Cl | Cl | (CH₂)₂OCH₃ |
| F | Cl | Cl | (CH₂)₂OCH₃ |
| H | Cl | Br | (CH₂)₂OCH₃ |
| F | Cl | Br | (CH₂)₂OCH₃ |
| H | Cl | CH₃ | (CH₂)₂OCH₃ |
| F | Cl | CH₃ | (CH₂)₂OCH₃ |
| H | Cl | CH₂CH₃ | (CH₂)₂OCH₃ |
| F | Cl | CH₂CH₃ | (CH₂)₂OCH₃ |
| H | Cl | H | CH(CH₃)CH₂OCH₃ |
| F | Cl | H | CH(CH₃)CH₂OCH₃ |
| H | Cl | Cl | CH(CH₃)CH₂OCH₃ |
| F | Cl | Cl | CH(CH₃)CH₂OCH₃ |
| H | Cl | Br | CH(CH₃)CH₂OCH₃ |
| F | Cl | Br | CH(CH₃)CH₂OCH₃ |
| H | Cl | CH₃ | CH(CH₃)CH₂OCH₃ |
| F | Cl | CH₃ | CH(CH₃)CH₂OCH₃ |
| H | Cl | CH₂CH₃ | CH(CH₃)CH₂OCH₃ |
| F | Cl | CH₂CH₃ | CH(CH₃)CH₂OCH₃ |
| H | Cl | H | CH₂CH=CH₂ |
| F | Cl | H | CH₂CH=CH₂ |
| H | Cl | Cl | CH₂CH=CH₂ |
| F | Cl | Cl | CH₂CH=CH₂ |
| H | Cl | Br | CH₂CH=CH₂ |
| F | Cl | Br | CH₂CH=CH₂ |
| H | Cl | CH₃ | CH₂CH=CH₂ |
| F | Cl | CH₃ | CH₂CH=CH₂ |
| H | Cl | CH₂CH₃ | CH₂CH=CH₂ |
| F | Cl | CH₂CH₃ | CH₂CH=CH₂ |
| H | Cl | H | CH₂CH=CHCH₃ |
| F | Cl | H | CH₂CH=CHCH₃ |
| H | Cl | Cl | CH₂CH=CHCH₃ |
| F | Cl | Cl | CH₂CH=CHCH₃ |
| H | Cl | Br | CH₂CH=CHCH₃ |
| F | Cl | Br | CH₂CH=CHCH₃ |
| H | Cl | CH₃ | CH₂CH=CHCH₃ |
| F | Cl | CH₃ | CH₂CH=CHCH₃ |
| H | Cl | CH₂CH₃ | CH₂CH=CHCH₃ |
| F | Cl | CH₂CH₃ | CH₂CH=CHCH₃ |
| H | Cl | H | CH₂C≡CH |
| F | Cl | H | CH₂C≡CH |
| H | Cl | Cl | CH₂C≡CH |
| F | Cl | Cl | CH₂C≡CH |
| H | Cl | Br | CH₂C≡CH |
| F | Cl | Br | CH₂C≡CH |
| H | Cl | CH₃ | CH₂C≡CH |
| F | Cl | CH₃ | CH₂C≡CH |
| H | Cl | CH₂CH₃ | CH₂C≡CH |
| F | Cl | CH₂CH₃ | CH₂C≡CH |
| H | Cl | H | CH₂C≡CCH₃ |
| F | Cl | H | CH₂C≡CCH₃ |
| H | Cl | Cl | CH₂C≡CCH₃ |
| F | Cl | Cl | CH₂C≡CCH₃ |
| H | Cl | Br | CH₂C≡CCH₃ |
| F | Cl | Br | CH₂C≡CCH₃ |
| H | Cl | CH₃ | CH₂C≡CCH₃ |
| F | Cl | CH₃ | CH₂C≡CCH₃ |
| H | Cl | CH₂CH₃ | CH₂C≡CCH₃ |
| F | Cl | CH₂CH₃ | CH₂C≡CCH₃ |
| H | Cl | H | CH₂Ph |
| F | Cl | H | CH₂Ph |

TABLE B-continued

Ib (structure: 4-methyl-tetrahydrophthalimido group attached to N of phthalimide-like ring, connected to phenyl bearing R¹, R², and CH=C(R³)(CO₂R⁴))

| R¹ | R² | R³ | R⁴ |
|---|---|---|---|
| H | Cl | Cl | CH₂Ph |
| F | Cl | Cl | CH₂Ph |
| H | Cl | Br | CH₂Ph |
| F | Cl | Br | CH₂Ph |
| H | Cl | CH₃ | CH₂Ph |
| F | Cl | CH₃ | CH₂Ph |
| H | Cl | CH₂CH₃ | CH₂Ph |
| F | Cl | CH₂CH₃ | CH₂Ph |
| H | F | Cl | CH₃ |
| H | F | Br | CH₃ |
| H | F | CH₃ | CH₃ |
| H | F | Cl | CH₂CH₃ |
| H | F | Br | CH₂CH₃ |
| H | F | CH₃ | CH₂CH₃ |
| H | F | Cl | (CH₂)₂CH₃ |
| H | F | Br | (CH₂)₂CH₃ |
| H | F | CH₃ | (CH₂)₂CH₃ |
| H | F | Cl | CH(CH₃)₂ |
| H | F | Br | CH(CH₃)₂ |
| H | F | CH₃ | CH(CH₃)₂ |
| H | F | Cl | (CH₂)₃CH₃ |
| H | F | Br | (CH₂)₃CH₃ |
| H | F | CH₃ | (CH₂)₃CH₃ |
| H | F | Cl | CH₂CH(CH₃)₂ |
| H | F | Br | CH₂CH(CH₃)₂ |
| H | F | CH₃ | CH₂CH(CH₃)₂ |
| H | F | Cl | (CH₂)₄CH₃ |
| H | F | Br | (CH₂)₄CH₃ |
| H | F | CH₃ | (CH₂)₄CH₃ |
| H | F | Cl | (CH₂)₂CH(CH₃)₂ |
| H | F | Br | (CH₂)₂CH(CH₃)₂ |
| H | F | CH₃ | (CH₂)₂CH(CH₃)₂ |
| H | F | Cl | (CH₂)₂OCH₃ |
| H | F | Br | (CH₂)₂OCH₃ |
| H | F | CH₃ | (CH₂)₂OCH₃ |
| H | F | Cl | CH(CH₃)CH₂OCH₃ |
| H | F | Br | CH(CH₃)CH₂OCH₃ |
| H | F | CH₃ | CH(CH₃)CH₂OCH₃ |
| H | F | Cl | CH₂CH=CH₂ |
| H | F | Br | CH₂CH=CH₂ |
| H | F | CH₃ | CH₂CH=CH₂ |
| H | F | Cl | CH₂CH=CHCH₃ |
| H | F | Br | CH₂CH=CHCH₃ |
| H | F | CH₃ | CH₂CH=CHCH₃ |
| H | F | Cl | CH₂CH≡CH |
| H | F | Br | CH₂CH≡CH |
| H | F | CH₃ | CH₂CH≡CH |
| H | F | Cl | CH₂C≡CCH₃ |
| H | F | Br | CH₂C≡CCH₃ |
| H | F | CH₃ | CH₂C≡CCH₃ |
| H | F | Cl | CH₂Ph |
| H | F | Br | CH₂Ph |
| H | F | CH₃ | CH₂Ph |

The 3-(N-3,4,5,6-tetrahydrophthalimido)-cinnamic esters I, and herbicidal and defoliating agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient. The active ingredients are employed in a purity of 90 to 100, and preferably 95 to 100, % (based on the NMR spectrum).

The compounds I according the invention may be formulated for instance as follows:

I. 90 parts by weight of compound no. 1.001 is mixed with 10 parts by weight of N-methyl-alpha-pyrrolidone. A mixture is obtained which is suitable for application in the form of very fine drops.

II. 20 parts by weight of compound no. 1.004 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1.003 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 1.005 is dissolved in a mixture consisting of 25 parts by weight of cyclohexanone, 65 parts by weight of a mineral oil fraction having a boiling point between 210° and 2800° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 1.004 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 1.001 is intimately mixed with 97 parts by weight of particulate kaolin. A dust is obtained containing 3% by weight of the active ingredient.

VII. 30 parts by weight of compound no. 1.004 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 1.002 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 3.0, preferably 0.01 to 1.0, kg of active ingredient per hectare.

The compounds I may also be used for the desiccation of cotton.

In view of the numerous application methods possible, the compounds according to the invention may be used in a large number of crops. Those which follow are given by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rapeseed |
| *Brassica napus* var. *napobrassica* | swedes |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora*, *Coffea liberica*) | coffee plants |
| *Cucumis melo* | melons |
| *Cucumis sativus* | cucumbers |
| *Cynodon dactylon* | Bermudagrass |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum*, *Gossypium herbaceum*, *Gossypium vitifolium*) | cotton |
| *Helianthus annuus* | sunflowers |
| *Helianthus tuberosus* | Jerusalem artichoke |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicotiana tabacum* (*N. rustica*) | tobacco |
| *Olea europaea* | olive trees |
| *Oryza sativa* | rice |
| *Panicum miliaceum* | millet |
| *Phaseolus lunatus* | limabeans |
| *Phaseolus mungo* | mungbeans |
| *Phaseolus vulgaris* | snapbeans, green beans, dry beans |
| *Pennisetum glaucum* | pearl millet |
| *Petroselinum crispum* spp. *tuberosum* | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |

-continued

| Botanical name | Common name |
| --- | --- |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Triticum durum | durum wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the 3-(N-3,4,5,6-tetrahydrophthalimido)-cinnamic esters I may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, (hetero)-aryloxyphenoxypropionic acids and salts, esters, amides thereof, etc.

It may also be useful to apply the novel compounds I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

Synthesis examples

The directions given in the synthesis examples below were employed, after appropriate modification of the starting materials, to obtain further compounds 1. The compounds thus obtained are listed with their physical data below.

EXAMPLE 1

Manufacture of
E/Z-N-[3-(2-methoxycarbonylprop-1-enyl)-4-chlorophenyl]-4(R,S)-methyl-3,4,5 6-tetrahydrophthalimide

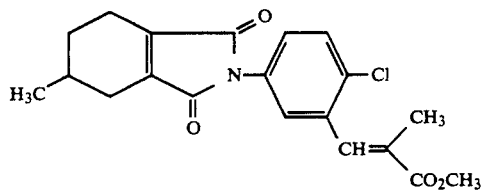

a) At 5° C., 167.4 g (1.8 mol) of α-picoline was added to a solution of 468 g (1.8 mol) of 2-chloro-5-nitro-α-methylcinnamyl chloride in 2250 ml of methanol. The reaction mixture was stirred for 12 hours at 23° C. After the mixture had been cooled to 0° C., the precipitate which formed was isolated and recrystallized from methanol. There was obtained 294 g (64%) of methyl 2-chloro-5-nitro-α-methylcinnamate (m.p. 95°–960° C).

b) 105 g (0.4 mol) of nitrocinnamyl ester was dissolved hot in 250 ml of methanol and 350 ml of glacial acetic acid, and the mixture was added, under reflux, to a mixture of 149 g of iron powder in 120 ml glacial acetic acid and the resultant mixture refluxed for 90 minutes. After cooling, the mixture was suction filtered, the filter residue was taken up in water and extracted three times with ethyl acetate, and the organic phases were washed with water, dried and evaporated down. There was obtained 81.1 g (88%) of methyl 2-chloro-5-amino-α-methylcinnamate (m.p. 800° C).

c) 4.5 g (0.02 mol) of the above aniline and 3.5 g (0.021 mol) of 4-methyl-cyclohexene-1,2-dicarboxylic anhydride were stirred for 17 hours in 120 ml of glacial acetic acid at 60° C., followed by concentration and recrystallization from methanol. There was obtained 4.7 g (63%) of the title compound (76°–780° C). (Table 1, No. 1.001)

EXAMPLE 2

Manufacture of
E/Z-N-[3-(2-chloro-2-methoxycarbonylethen-1-yl)-4-chloro-phenyl]-4(R,S)-methyl-3,4,5,6-tetrahydrophthalimide

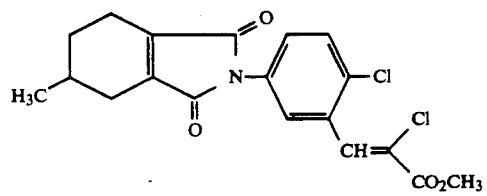

a) 29.2 g (0.15 mol) of 4-chloro-(1,3-dioxolan-2-yl)-aniline and 24.9 g (0.15 mol) of 4(R,S)-methylcyclohexene-1,2-dicarboxylic anhydride were stirred in 250 ml of glacial acetic acid for 3 days at 230° C. and for 10 hours at 70° C.; water was added to induce precipitation, followed by recrystallization and drying. There was obtained 38 g (83%) of N-(4-chloro-3-formylphenyl)-4(R,S)-methyl-3,4,5,6-tetrahydrophthalimide (m.p. 132°–1330° C.).

b) 3 g (0.01 mol) of the above aldehyde and 3.7 g (0.01 mol) of carbomethoxychloromethylene triphenylphosphorane in 50 ml of methanol were stirred for 5 hours at 230° C. After the addition of 25 mol of water the precipitate was suction filtered, washed with ligroin and dried. There was obtained 3.0 g (76%) of the title compound (m.p. 91°–920° C.) (Table 1, No. 1.004).

TABLE 1

| Act. Ingr. No. | $R^1$ | $R^2$ | $R^3$ | $R^4$ | $(R)_n$ | Phys. data mp (°C.); IR (cm$^{-1}$) |
| --- | --- | --- | --- | --- | --- | --- |
| 1.001 | H | Cl | $CH_3$ | $CH_3$ | 4-$CH_3$ | 76–78 |

TABLE 1-continued

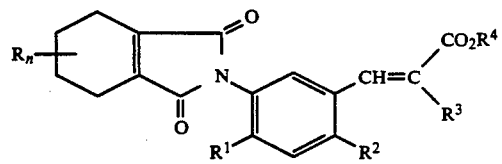

| Act. Ingr. No. | $R^1$ | $R^2$ | $R^3$ | $R^4$ | $(R)_n$ | Phys. data mp (°C.); IR (cm$^{-1}$) |
|---|---|---|---|---|---|---|
| 1.002 | H | Cl | Br | CH$_3$ | 4-CH$_3$ | 95–96 |
| 1.003 | H | Cl | Br | CH$_2$CH$_3$ | 4-CH$_3$ | 72–73 |
| 1.004 | H | Cl | Cl | CH$_3$ | 4-CH$_3$ | 91–92 |
| 1.005 | H | Cl | Cl | CH$_2$CH$_3$ | 4-CH$_3$ | 82–83 |
| 1.006 | H | Cl | CH$_3$ | CH$_2$CH$_3$ | 4-CH$_3$ | 1714, 1474, 1376, 1255 |
| 1.007 | H | Cl | Br | C(CH$_3$)$_3$ | 4-CH$_3$ | 97–98 |
| 1.008 | H | Cl | Br | CH(CH$_3$)$_2$ | 4-CH$_3$ | 105–106 |
| 1.009 | H | Cl | Cl | C(CH$_3$)$_3$ | 4-CH$_3$ | 118–119 |
| 1.010 | H | Cl | Cl | CH(CH$_3$)$_2$ | 4-CH$_3$ | 120–121 |
| 1.011 | F | Cl | Br | CH$_3$ | 4-CH$_3$ | 125–126 |
| 1.012 | F | Cl | Cl | CH$_2$CH$_3$ | 4-CH$_3$ | 1721, 1488, 1419, 1238 |
| 1.013 | F | Cl | Cl | CH$_3$ | 4-CH$_3$ | 1721, 1489, 1420, 1241 |

USE EXAMPLES

The herbicidal action of the 3-(N-3,4,5,6-tetrahydrophthalimido)-cinnamic esters of the formula I is demonstrated in greenhouse experiments:

The vessels employed were plastic flowerpots having a volume of 300 cm$^3$ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 15 cm before being treated with the compounds, suspended or emulsified in water. The application rates for post-emergence treatment were 0.03 and 0.06 kg/ha.

The pots were set up in the greenhouse, heat-loving species at 20° to 350° C., and species from moderate climates at 10° to 200° C. The experiments were run for from 2 to 4 weeks. During this period the plants were tended and their reactions to the various treatments assessed. The assessment scale was 0 to 100, 100 denoting nonemergence or complete destruction of at least the visible plant parts, and 0 denoting no damage or normal growth.

The plants employed for the experiments were *Abutilon theophrasti, Amaranthus retroflexus, Chrysanthemum corinarium, Oryza sativa* and *Solanum nigrum*.

Compounds 1.001, 1.004 and 1.005, applied postemergence at a rate of 0.03 and 0.06 kg/ha, provided excellent control of unwanted broadleaved plants, and compound 1.001 was also tolerated by rice.

We claim:

1. A 3-(N-3,4,5,6-Tetrahydrophthalimido)-cinnamic ester of the formula I where $R^1$ is hydrogen or fluorine, $R^2$ is halogen, $R^3$ is hydrogen, halogen or $C_1$–$C_4$-alkyl, $R^4$ is hydrogen, $C_1$–$C_6$-alkyl which can be substituted by one or two $C_1$–$C_4$-alkoxy or $C_1$–$C_4$-alkylthio groups, or $C_3$–$C_7$-cycloalkyl, $C_3$–$C_6$-alkenyl, $C_3$–$C_6$-alkynyl or benzyl, R is $C_1$–$C_4$-alkyl, and n is 1 or 2.

2. A herbicidal composition which comprises an inert carrier and a herbicidally effective amount of a 3-(N-3,4,5,6-tetrahydrophthalimido)-cinnamic ester of the formula I as set forth in claim 1.

3. A method of combating the growth of unwanted plants which comprises: applying to unwanted plants or their habitat a herbicidally effective amount of a 3-(N-3,4,5,6-tetrahydrophthalimido)-cinnamic ester I as set forth in claim 1.

4. A method of defoliating cotton plants which comprises: applying to the cotton plants a defoliating amount of a 3-(N-3,4,5,6-tetrahydrophthalimido)-cinnamic ester I as set forth in claim 1.

* * * * *